(12) United States Patent
Kim et al.

(10) Patent No.: US 7,449,574 B2
(45) Date of Patent: Nov. 11, 2008

(54) TRIAZINE BASED PHOTOACTIVE COMPOUND CONTAINING OXIME ESTER

(75) Inventors: Sung Hyun Kim, Daejeon Metropolitan (KR); Jeong Ae Yoon, Masan-si (KR); Raisa Kharbash, Daejeon Metropolitan (KR); Han Soo Kim, Seoul (KR); Xiang Li Li, Daejeon Metropolitan (KR); Min Young Lim, Daejeon Metropolitan (KR); Chang Ho Cho, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 11/593,051

(22) Filed: Nov. 6, 2006

(65) Prior Publication Data

US 2007/0106075 A1   May 10, 2007

(30) Foreign Application Priority Data

Nov. 7, 2005   (KR) .................. 10-2005-0106157

(51) Int. Cl.
*C07D 251/24* (2006.01)
*C08F 2/46* (2006.01)
*G03C 1/675* (2006.01)
*G03C 1/73* (2006.01)

(52) U.S. Cl. .................. 544/180; 544/193; 544/216; 430/281.1; 430/920

(58) Field of Classification Search .......... 544/180, 544/193, 216
See application file for complete search history.

(56) References Cited

U.S. PATENT DOCUMENTS

| 4,202,697 A | 5/1980 | Van Goethem et al. |
| 4,255,513 A | 3/1981 | Laridon et al. |
| 4,391,687 A | 7/1983 | Vesley |
| 4,590,145 A | 5/1986 | Itoh et al. |
| 4,837,128 A | 6/1989 | Kawamma et al. |
| 5,298,361 A | 3/1994 | Bonham |
| 5,776,996 A | 7/1998 | Okamoto et al. |
| 6,001,517 A | 12/1999 | Kawamonzen |
| 6,051,367 A | 4/2000 | Kunita et al. |
| 6,261,738 B1 | 7/2001 | Asakura et al. |
| 2005/0191567 A1 | 9/2005 | Kunimoto et al. |

FOREIGN PATENT DOCUMENTS

| DE | 19928742 A1 | 12/1999 |
| EP | 271 195 B1 | 6/1988 |
| JP | 53-133428 | 11/1978 |
| JP | 61-118423 | 6/1986 |
| JP | 63-070243 | 3/1988 |
| JP | 64-068750 | 3/1989 |
| JP | 03-004226 | 1/1991 |
| KR | 1020000056234 A | 9/2000 |
| WO | WO 00/52530 | 9/2000 |
| WO | WO 02/100903 A1 | 12/2002 |
| WO | WO 2004/050653 A1 | 6/2004 |

OTHER PUBLICATIONS

Ingwaii et al, "Hologram recording with a new potopolymer system", Optical Engineering, Sep./Oct. 1985, vol. 24 No. 5, pp. 808-811.
Kirsch et al., "Design of photopolymer holograms for optical interconnect application", Optical Engineering, Apr. 1988, vol. 27 No. 4, pp. 301-308.Kirsch et al., "Design of photpolymer holograms for optical interconnect application", Optical Engineering, Apr. 1988, vol. 27 No. 4, pp. 301-308.Kirsch et al., "Design of photpolymer holograms for optical interconnect application", Optical Engineering, Apr. 1988, vol. 27, No. 4, pp. 301-308.

*Primary Examiner*—Venkataraman Balasubram
(74) *Attorney, Agent, or Firm*—McKenna Long & Aldridge LLP

(57) ABSTRACT

The present invention relates to a triazine based photoactive compound containing an oxime ester group.

The compound according to the present invention is a photoactive compound containing both an oxime ester group and a triazine group in one molecule, has excellent radical-generating efficiency due to effective absorption of UV radiation, particularly i-line (365 nm) radiation and can function as an effective initiator for photopolymerization of various compounds containing unsaturated groups, particularly an acryl compound.

2 Claims, No Drawings

TRIAZINE BASED PHOTOACTIVE COMPOUND CONTAINING OXIME ESTER

TECHNICAL FIELD

The present invention relates to a triazine based photoactive compound containing oxime ester.

The present application claims the benefit of Korean Patent Application No. 2005-0106157 (filed on Nov. 7, 2005), which is incorporated herein by its entirety for reference.

BACKGROUND ART

A photosensitive composition can be applied onto a substrate to form a coating film, a specific portion of the coating film is subjected to exposure by light irradiation using a photomask and then a non-exposure portion is subjected to a development treatment to remove it, thereby forming a pattern. This photosensitive composition have been used for photocurable inks, photosensitive printing plates, various photoresists, color filter photoresists for LCD, photoresists for resin black matrix, transparent photosensitive materials and the like since the photosensitive composition can be polymerized and cured by light irradiation.

The photosensitive composition usually contains an alkali-soluble resin, a polymerizable compound having an ethylenically unsaturated bond, a photopolymerization initiator and a solvent.

As the photopolymerization initiator used in the photosensitive composition, there have been known various types such as acetophenone derivatives, benzophenone derivatives, biimidazole derivatives, acylphosphine oxide derivatives, triazine derivatives and oxime derivatives.

Among these, the oxime derivatives have advantages that are almost never in color, and have high permeability, high radical-generating efficiency by UV irradiation, and excellent stability and compatibility in the composition.

Japanese Patent Application Laid-Open (JP-A) No. 61-118423, JP-A No. 1-68750 and JP-A No. 3-4226 disclose the use of α-oxooxime derivatives as a photoresist photoinitiator for photoimaging and printed wiring board, and Opt. Eng. 24 (1985) 808 and J. Opt. Eng. 27 (1988) 301 discloses the use of α-oxooxime derivatives as a photoinitiator for holography.

In particular, with regard to a photoinitiator having the structure of an oxime ester, U.S. Pat. No. 4,590,145 discloses a photoinitiation system comprising thioxanthone and an oxime ester compound, U.S. Pat. No. 4,255,513 discloses an oxime ester photoinitiation system containing p-dialkylaminobenzene used as a synergist, U.S. Pat. No. 5,776,996 discloses a photoinitiator comprising β-aminooxime with a sensitizing dye and a titanocene compound, and U.S. Pat. No. 6,051,367 discloses an oxime ether photoinitiation system having ethylenically unsaturated bonds capable of participating in the photopolymerization in the molecular structure. WO 00/52530 and German Patent Application Laid-Open No. 199 28 742 A1 describe a photosensitive composition using oxime ether, oxime ester, and particularly oxime sulfonate as a photoinitiator. WO 02/100903 A1 describes an oxime ester compound having a structure bonded with alkyl acyl ketone, diaryl ketone or ketocoumarine.

In addition to these compounds, U.S. Pat. No. 4,202,697 describes an etch resist having an oxime ester structure and U.S. Pat. No. 6,001,517 describes a positive photosensitive composition comprising an oxime ester structure as a photosensitive cure accelerator.

However, among the oxime derivative compounds used as above, the initially developed compounds have low photoinitiation efficiency and do not effective for UV-light absorption in the case of having good color properties. The oxime derivative compounds published since the latter half of the 1990s have very good improved photoinitiation efficiency, but do not sufficiently satisfy the processing time conditions that were recently tightened. In particular, the oxime derivative compounds still has difficulties in the formation of fine patterns since thick films having a high concentration pigment or a coating thickness of 2.5 μm or more have no sufficient curing degree, and patterns formed therefrom cannot exhibit CD (critical dimension) and mechanical strength required for products.

Meanwhile, a halomethyl triazine compound, which generates halogen radical when decomposed by light irradiation, has also frequently been used as the photopolymerization initiator. In particular, it is known that 2-aryl-4,6-bis(trihalomethyl)-s-triazine has relatively good sensitivity.

For example, JP-A No. 53-133428 describes the use of a triazine based compound having a bicyclic or polycyclic aromatic group or heterocyclic aromatic group, particularly preferably a naphthyl group, as an aryl group at the 2-position thereof. The triazine based compound has unsatisfactory sensitivity in the practical applications and it is required to be used in large quantities and to be irradiated by light in long-term. And it has disadvantages in that the stability of a photosensitive composition with time is lowered because of insufficient solubility into a polymerizable compound having ethylenically unsaturated bonds.

Furthermore, although it is disclosed in JP-A No. 63-70243 that the stability with time of a photosensitive composition can be improved by introducing substituents having amide bonds or ester bonds into a naphthyl group at the 2-position of a triazine based compound, the sensitivity as a photoinitiator was not satisfactory since the initiator having low molecular weight and high crystallinity is precipitated onto the coated film surface or crystallizes in the film after coating.

Known methods used to solve these problems include using initiators having strong interactions with binders, photoinitiators with large molecular weights, and multi-functional or poly-functional triazine based photoinitiators.

In conjunction with the above methods, a photoinitiator having two or more photoactive triazine groups is disclosed in U.S. Pat. No. 5,298,361. 2-Aryl-4,6-bis(trihalomethyl)-s-triazine based derivatives in which an amino group substituted phenyl group is introduced at the 2-position are disclosed in U.S. Pat. No. 4,837,128. However, these compounds have excellent photoactivities, but have limits in the applications requiring color purity since they have maximum absorbance at 350 nm or more and absorb light within the scope of visible rays. Furthermore, 2-aryl-4,6-bis(trihalomethyl)-s-triazine based derivatives in which phenyl groups coupled with simple alkyl or aryl groups by S, Se, or Te are introduced at the 2-position are disclosed in European Patent Application Laid-Open No. 271195 A1. However, these compounds have problems of compatibility with binders used in a photosensitive composition, and of sublimation in the high temperature process when alkyl groups having less carbon atoms are substituted.

Therefore, it has been desired the development of a photoinitiator having advantages of both the oxime ester compound and the triazine based compound, capable of effectively absorbing UV radiation and having excellent sensitivity and excellent high temperature process characteristics.

Disclosure

[Technical Problem]

In this regard, the present inventors have investigated a photoinitiator having advantages of both an oxime ester compound and a triazine based compound and have synthesized a compound having a specific structure of introducing both an oxime ester group and a triazine group in one molecule. As a result, the present inventors have found that this compound is capable of effectively absorbing UV radiation and has excellent sensitivity and excellent high temperature process characteristics and have completed the present invention.

[Technical Solution]

It is an object of the present invention to provide a triazine based photoactive compound containing oxime ester.

It is another object of the present invention to provide a method for producing a triazine based photoactive compound containing oxime ester.

[Advantageous Effects]

The compound according to the present invention is a photoactive compound containing both an oxime ester group and a triazine group in one molecule, has excellent radical-generating efficiency due to effective absorption of UV radiation, particularly i-line (365 nm) radiation and can function as an effective initiator for photopolymerization of various compounds containing unsaturated groups, particularly an acryl compound.

[Best Model]

The present invention provides a triazine based photoactive compound containing oxime ester represented by the following formula (1):

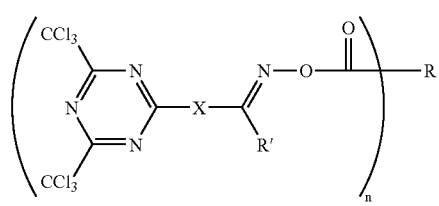

wherein n is an integer of 1 or 2;

when n=1, R is selected from the group consisting of a $C_1$ to $C_6$ alkyl group, a $C_1$ to $C_6$ haloalkyl group, a $C_1$ to $C_6$ alkyl group substituted with one or more groups selected from the group consisting of $NL_2$, OL and SL wherein L is a hydrogen atom or $C_1$ to $C_6$ alkyl group, a phenyl group unsubstituted or substituted with one or more groups selected from the group consisting of a $C_1$ to $C_6$ alkyl group, a halogen atom, a nitrile group, OH and COOH, and a $C_2$ to $C_5$ alkylcarboxyl group;

when n=2, R is selected from the group consisting of a $C_2$ to $C_6$ alkylene group, a 1,2-phenylene group, a 1,3-phenylene group, 1,4-phenylene group,

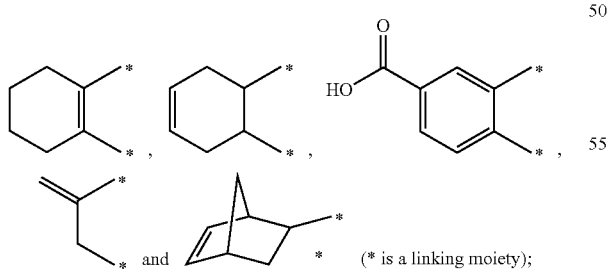

(* is a linking moiety);

R' is selected from the group consisting of a hydrogen atom, a $C_1$ to $C_6$ alkyl group, a nitrile group and a phenyl group;

X is a $C_5$ to $C_{20}$ arylene group unsubstituted or substituted with one or more groups selected from the group consisting of a halogen atom, CN, a $C_1$ to $C_6$ alkyl group, a $C_1$ to $C_6$ alkoxy group, a $C_1$ to $C_6$ alkylthio group and a morpholino group; a divalent $C_4$ to $C_{20}$ heterocyclic group containing O, N or S, unsubstituted or substituted with one or more groups selected from the group consisting of a halogen atom, CN, a $C_1$ to $C_6$ alkyl group, a $C_1$ to $C_6$ alkoxy group, a $C_1$ to $C_6$ alkylthio group and a morpholino group; or a compound of the following formula (2):

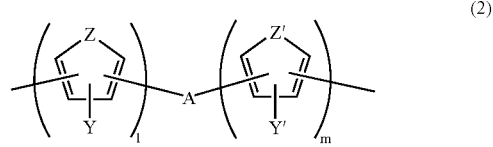

wherein Z and Z' are each independently selected from the group consisting of $CH_2$, O, S, NR'' wherein R'' is a hydrogen atom or $C_1$ to $C_6$ alkyl group, and CH=CH;

l and m are an integer of 0 to 2, provided that l+m is not 0;

A is a simple linkage, or one selected from the group consisting of $C_pH_{2p}$, $O(CH_2O)_p$, CH=CH, NR''', S, O, S=O, $SO_2$, and C=O wherein p is an integer of 1 to 6 and R''' is a hydrogen atom or $C_1$ to $C_6$ alkyl group, provided that A is not a simple linkage when l+m=1; and Y and Y' are each optionally selected from the group consisting of a hydrogen atom, a halogen atom, CN, a $C_1$ to $C_6$ alkyl group, a $C_1$ to $C_6$ alkoxy group, a $C_1$ to $C_6$ alkylthio group and a morpholino group.

Preferably in the formula (1), when n=1, R is a methyl group or a phenyl group;

when n=2, R is an ethylene group or a tetrahydrophthalene group;

R' is a hydrogen atom, a methyl group or a phenyl group; and

X is selected from the group consisting of a phenylene group, a biphenylene group, a styrylene group and the following structural formulae:

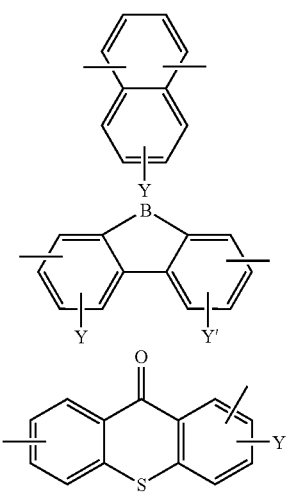

wherein B is one selected from the group consisting of $CH_2$, O, S, NR'' wherein R'' is a hydrogen atom or $C_1$ to $C_6$ alkyl group, and CH=CH; and Y and Y' are each optionally selected from the group consisting of a hydrogen atom, a halogen atom, CN, a $C_1$ to $C_6$ alkyl group, a $C_1$ to $C_6$ alkoxy group, a $C_1$ to $C_6$ alkylthio group and a morpholino group.

More preferably, in the formula (1), X is a phenylene group, a biphenylene group or a styrylene group.

In the formula (1), R is a moiety decomposed into radicals as active species upon exposure and is not particularly structurally limited, but the simpler structure the more movable, thereby improving photoinitiation efficiency.

X has to have a structure capable of absorbing UV radiation, particularly light in the 260 nm to 440 nm region, but is not particularly limited as long as it can have absorbance function. X is particularly preferable an aromatic group because of characteristics of the absorption wavelength band.

Further, the present invention provides a method for producing a triazine based photoactive compound containing oxime ester, represented by the following formula (1).

The method according to the present invention comprises the steps of:

1) reacting a carbonyl-triazine compound (A) with hydroxyamine hydrochloride (NH$_4$OH.HCl) in the presence of a base to convert a carbonyl group to an oxime group and thus to prepare an oxime-triazine compound (B); and 2) reacting the oxime-triazine compound (B) prepared in the above 1) with carboxylic anhydride or carboxylic chloride to convert the oxime group to an oxime ester group and thus to prepare a triazine based photoactive compound (C) containing the oxime ester group.

The method is described in detail in a step-by-step manner in the following.

The carbonyl-triazine compound (A) used as a starting material in the above 1) can be prepared by two methods:

A first method is a method in which a compound (D) having both a carbonyl group and a nitrile group in the molecule is condensed with trichloroacetonitrile in the presence of a catalyst.

1 eq. of carbonyl-nitrile compound (D) and 2 eq. of trichloroacetonitrile can be subjected to a cyclization reaction in the presence of a catalyst to prepare a bis(trichloromethyl)triazine cyclic compound. In this case, the catalysts used are Lewis acids such as aluminum chloride and aluminum bromide and the hydrogen chloride gas required in the cyclization reaction is provided in the dry state. The hydrogen chloride gas can be used by drying one generated after dropping hydrochloric acid (35% aqueous solution) into conc. sulfuric acid, but for convenience the hydrogen chloride gas can be also provided in a bombe. The solvent used in the reaction includes anhydrous diethyl ether, anhydrous tetrahydrofuran (THF) and anhydrous methylene chloride. It is most preferable to use an excess of trichloroacetonitrile of 10 mole equivalents or more to function as a solvent and the reactant since the reaction is easily occurred when a high concentration of trichloroacetonitrile is used. In the reaction, the carbonyl group may be chlorinated under strong acidic conditions. In this case, it is treated with conc. sulfuric acid to regenerate the carbonyl group.

A second method is a method of oxidizing an alkyl group of the compound (E) having both an alkyl group and a triazine group substituted in an aromatic compound.

When an aromatic group is substituted with an alkyl group, an alkylene group or alkyl group next to the aromatic group is readily oxidized. Examples of the oxidation method include a direct oxidation method and an indirect oxidation method.

The direct oxidation method includes 1) a method of using KMnO$_4$/CuSO$_4$.5H$_2$O in a methylene chloride solvent, 2) a method of using KMnO$_4$/MgSO$_4$ in a mixed solvent of t-butyl alcohol/water, and 3) a method of using KMnO$_4$/MnO$_2$ in a nitric acid solvent. However, the direct oxidation method may generate side reaction such as decomposition of the compound (E) since it is carried out under relatively severe conditions.

Therefore, the indirect oxidation method in which the alkyl group of the compound (E) is halogenated and then oxidized is more preferable than the direct oxidation method.

In order to halogenate the alkyl group of the compound (E), it is preferable to use NBS (N-bromosuccinimide) and AIBN (azobisisobutyronitrile) as radical compounds and use a halogen solvent such as carbon tetrachloride (CCl$_4$). Then, a method of stirring with silver nitrate (AgNO$_3$) in a mixed solvent of ethanol and water under reflux, or a method of stirring with hexamethylenetetramine in chloroform and then in a 5% aqueous HCl solution or 50% aqueous acetic acid solution under reflux can be used.

The method for producing the starting material is a schematic method for the compound of the present invention and the reaction conditions may be varied depending on the structure of each compound, characteristic features and properties. Further, various methods for producing the compound (D) or compound (E) are provided and a commercially available reagent can also be used, when necessary.

The base used in the above 1) is sodium hydroxide or sodium acetate and may be used by diluting with a suitable amount of water. In this case, since the oxime-triazine compound (B) is not dissolved in water, an alcoholic solvent such as methanol, ethanol and isopropanol may be used as the solvent. In particular, ethanol is most preferable in terms of affinity with water, exothermic heat during reaction, toxicity and the like.

The esterification reaction in the above 2) is preferably carried out at low temperature because the oxime-triazine compound (B) may be damaged when alcohol and carboxylic acid are simply heated at high temperature of about 120° C. under basic condition.

Therefore, the oxime-triazine compound (B) is reacted with carboxylic anhydride or carboxylic chloride and amine is added as a basic compound so that hydrochloric acid or carboxylic acid generated in the reaction, can be removed in the form of a salt thereof. The amine added is preferably triethylamine or pyridine, but is not particularly limited thereto. In this case, the solvent used is not particularly limited as long as it does not have an alcoholic group. The solvent used is preferably an anhydrous solvent in which the oxime-triazine compound (B) is well dissolved and a salt formed as a by-product is not dissolved. Specific examples of the solvent include dichloromethane, chloroform, tetrahydrofuran, diethyl ether and ethyl acetate.

[Mode for Invention]

A better understanding of the present invention may be had from the following Examples. It should be understood that Examples are given for purpose of illustration and are not considered as limiting the scope of this invention.

EXAMPLE 1

Preparation of 2,4-trichloromethyl-(4'-formylphenylacetoxime)-6-triazine (1)

(1) Preparation of 2,4-trichloromethyl-(4'-dichloromethylphenyl)-6-triazine (1a)

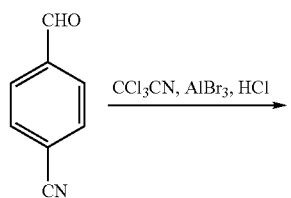

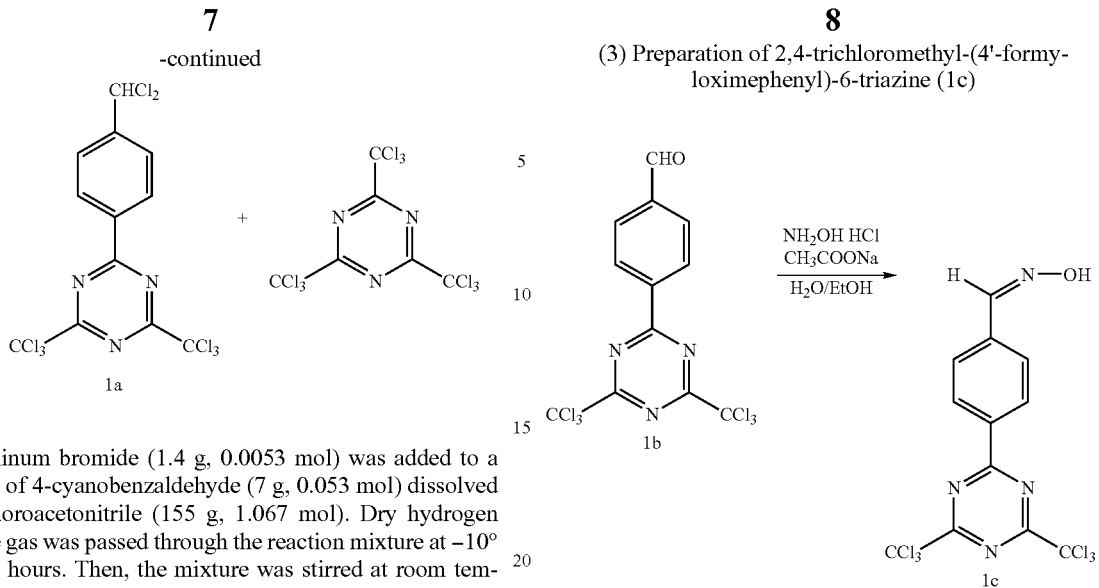

Aluminum bromide (1.4 g, 0.0053 mol) was added to a solution of 4-cyanobenzaldehyde (7 g, 0.053 mol) dissolved in trichloroacetonitrile (155 g, 1.067 mol). Dry hydrogen chloride gas was passed through the reaction mixture at −10° C. for 2 hours. Then, the mixture was stirred at room temperature for one day. Trichloroacetonitrile was removed under reduced pressure. The residue was treated with n-hexane to obtain 2,4-trichloromethyl-(4'-dichloromethylphenyl)-6-triazine (1a). Yield: 15 g (60%)

$^1$H NMR (500 MHz, acetone-$d_6$, ppm) 8.81-8.79 (2H, d, ArH), 7.99-7.98 (2H, d, ArH), 6.82 (1H, s, CHCl$_2$).

(2) Preparation of 2,4-trichloromethyl-(4'-formylphenyl)-6-triazine (1b)

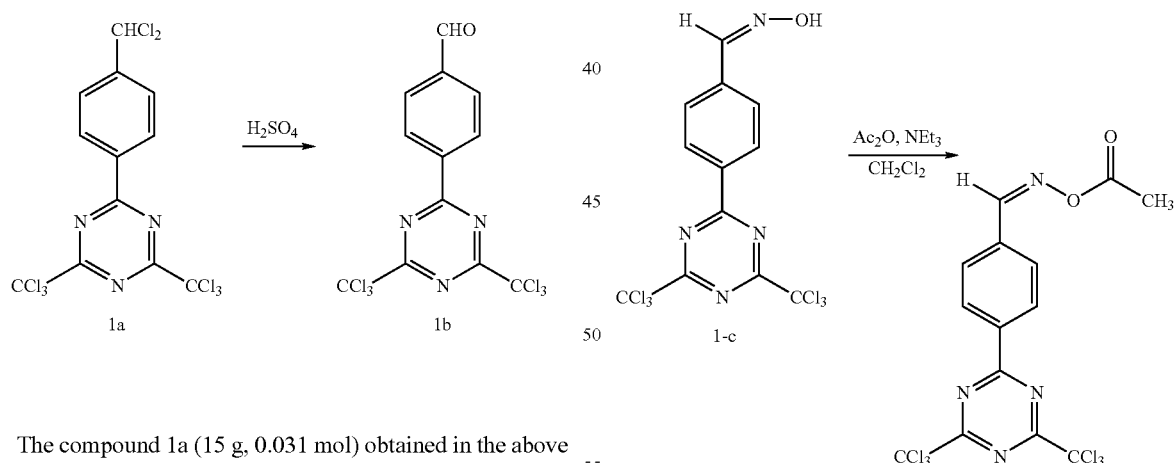

The compound 1a (15 g, 0.031 mol) obtained in the above (1) was hydrolyzed under conc. sulfuric acid (120 g) and was reacted at room temperature for 2 hours. The whole reaction mixture was poured into ice water and the product was extracted with ethyl acetate. The organic layer was washed with concentrated sodium bicarbonate and then dried over magnesium sulfate. The solvent was removed under reduced pressure and the residue was passed through a short column (hexane/ethyl acetate=3/1). As a result, 2,4-trichloromethyl-(4'-formylphenyl)-6-triazine (1b) was obtained. Yield: 8.3 g (63%).

$^1$H NMR (500 MHz, acetone-$d_6$, ppm) 10.25 (1H, s, CHO), 8.90-8.88 (2H, d, ArH), 8.25-8.23 (2H, d, ArH).

(3) Preparation of 2,4-trichloromethyl-(4'-formyloximephenyl)-6-triazine (1c)

A solution of the compound 1b (2.5 g, 5.9 mmol) obtained in the above (2), dissolved in ethanol (30 ml) was added to a solution of hydroxyamine hydrochloride (0.45 g, 6.5 mmol) and sodium acetate (0.62 g, 7.6 mmol) dissolved in water (10 ml). This reaction mixture was stirred under reflux for 1 hour. The reaction was confirmed by TLC (hexane/ethyl acetate=3/1). Water (200 ml) was added to the reaction mixture. 2,4-Trichloromethyl-(4'-formyloximephenyl)-6-triazine (1c) formed as a white solid was filtered, washed with water and then dried. Yield: 2.3 g (92%).

$^1$H NMR (500 MHz, acetone-$d_6$, ppm) 10.85 (1H, s, NOH), 8.72-8.70 (2H, d, ArH), 8.32 (1H, s, H—C=N), 7.95-7.93 (2H, d, ArH).

(4) Preparation of 2,4-trichloromethyl-(4'-formylphenylacetoxime)-6-triazine (1)

Acetic anhydride (0.59 g, 5.8 mmol) was added to a solution of the compound 1c (2.3 g, 5.2 mmol) obtained in the above (3) and triethylamine (0.58 g, 5.8 mmol) dissolved in dichloromethane (20 ml) and the reaction mixture was at room temperature stirred for one day. Then, the solvent was removed under reduced pressure and the product was treated with ethanol to obtain the target compound 1. Yield: 1.3 g (54%).

$^1$H NMR (500 MHz, CDCl$_3$, ppm) 8.76-8.74 (2H, d, ArH), 8.47 (1H, s, H—C=N), 7.97-7.95 (2H, d, ArH), 2.27 (3H, s, O=CCH$_3$).

EXAMPLE 2

Preparation of 2,4-trichloromethyl-(4'-acetylphenylacetoxime)-6-triazine (2)

(1) Preparation of 2,4-trichloromethyl-(4'-acetylphenyl)-6-triazine (2a)

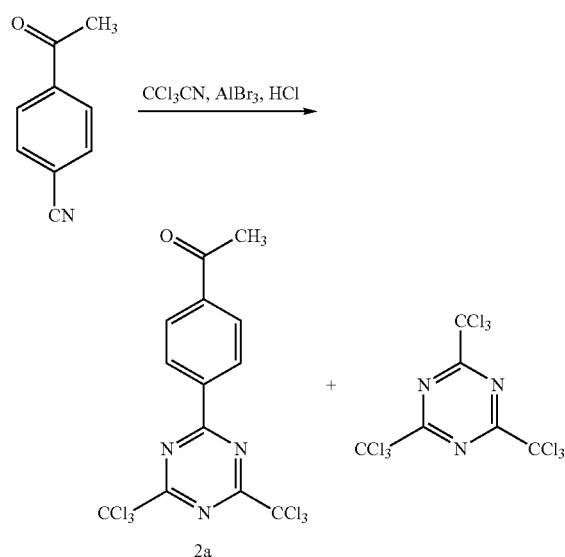

Aluminum bromide (0.9 g, 0.0034 mol) was added to a solution of 4-cyanobenzaldehyde (5 g, 0.034 mol) dissolved in trichloroacetonitrile (100 g, 0.688 mol). Dry hydrogen chloride gas was passed through the reaction mixture at −10° C. for 2 hours. Then, the mixture was stirred at room temperature for one day. Trichloroacetonitrile was removed under reduced pressure. As a result, the mixture of 2,4-trichloromethyl-(4'-acetylphenyl)-6-triazine (2a) and 2,4,6-tris(trichloromethyl)-1,3,5-triazine as a by-product was formed. The products were not separated since they have similar solubility in any solvent.

$^1$H NMR (500 MHz, CDCl$_3$, ppm) 8.80-8.78 (2H, d, ArH), 8.15-8.14 (2H, d, ArH), 2.70 (3H, s, O=CCH$_3$).

(2) Preparation of 2,4-trichloromethyl-(4'-acetylphenyloxime)-6-triazine (2b)

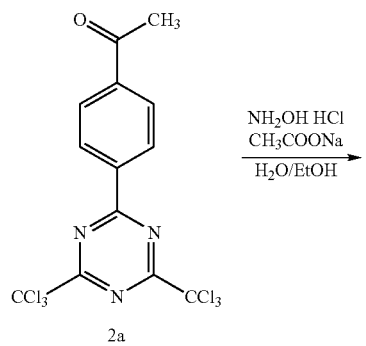

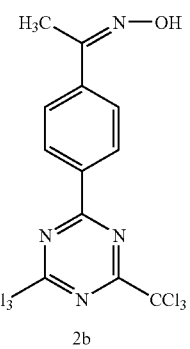

A solution of the compound 2a obtained in the above (1) and 2,4,6-tris-trichloromethyl-1,3,5-triazine (7.6 g) dissolved in ethanol (90 ml) was added to a solution of hydroxyamine hydrochloride (1.3 g, 19.2 mmol) and sodium acetate (1.8 g, 22.7 mmol) dissolved in water (30 ml). The reaction mixture was stirred under reflux for 1 hour. The reaction was confirmed by TLC (hexane/ethyl acetate=3/1). After the reaction was completed, 2,4,6-tris-trichloromethyl-1,3,5-triazine was filtered off and water (500 ml) was added to the filtrate. The formed 2,4-trichloromethyl-(4'-acetylphenyl oxime)-6-triazine (2b) was filtered, washed with water and then dried. Yield: 4.7 g.

$^1$H NMR (500 MHz, CDCl$_3$, ppm) 8.70-8.69 (2H, d, ArH), 8.01 (1H, s, NOH), 7.87-7.85 (2H, d, ArH), 2.35 (3H, s, —N=CCH$_3$).

(3) Preparation of 2,4-trichloromethyl-(4'-acetylphenylacetoxime)-6-triazine (2)

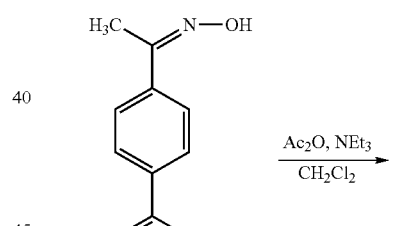

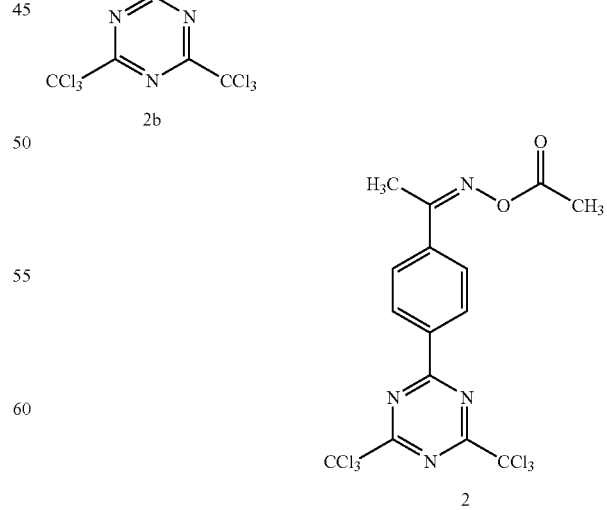

Acetic anhydride (1.1 g, 11.5 mmol) was added to a solution of the compound 2b (4.7 g, 10.4 mmol) obtained in the above (2) and triethylamine (1.1 g, 11.5 mmol) dissolved in dichloromethane (60 ml) and the reaction mixture was stirred at room temperature for one day. Then, the solvent was removed under reduced pressure and the product was treated with ethanol to obtain the target compound 2. Yield: 2.3 g (45%).

$^1$H NMR (500 MHz, CDCl$_3$, ppm) 8.73-8.71 (2H, d, ArH), 7.98-7.96 (2H, d, ArH), 2.46 (3H, s, O=CCH$_3$), 2.30 (3H, s, —N=CCH$_3$).

EXAMPLE 3

Preparation of 2,4-trichloromethyl-(4'-formylacetoximestyryl)-6-triazine (3)

(1) Preparation of 2,4-trichloromethyl-(4'-methylstyryl)-6-triazine (3a)

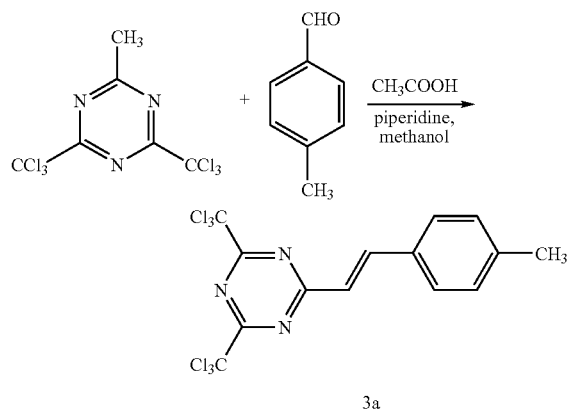

3a

Acetic acid (1.7 g, 29.3 mmol) and piperidine (2 g, 24.4 mmol) were added to a solution of 2-methyl-4,6-bis-trichloromethyl-1,3,5-triazine (13.7 g, 41.6 mmol) and para-tolualdehyde (5 g, 41.6 mmol) dissolved in methanol (100 ml). The reaction mixture was stirred under reflux for 6 hours. The reaction was confirmed by TLC (eluent: dichloromethane). After the reaction was completed, the precipitate was filtered, washed with methanol and then dried. As a result, 2,4-trichloromethyl-(4'-methylstyryl)-6-triazine (3a) was obtained. Yield: 12.6 g (70%).

$^1$H NMR (500 MHz, DMSO, ppm) 8.38-8.35 (1H, d, CH=), 7.85-7.83 (2H, d, ArH), 7.49-7.45 (1H, d, =CH), 7.31-7.30 (2H, d, ArH), 2.36 (1H, s, CH$_3$).

(2) Preparation of 2,4-trichloromethyl-(4'-bromomethylstyryl)-6-triazine (3b)

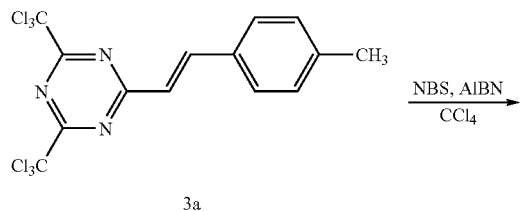

3a

-continued

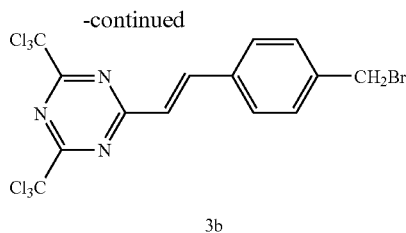

3b

N-Bromosuccinimide (4.1 g, 23.1 mmol) and 2,2'-azobis-butyronitrile (0.2 g) were added to a solution of the compound 3a (5 g, 11.5 mmol) obtained in the above (1) dissolved in carbon tetrachloride (50 ml). The reaction mixture was stirred under reflux for 2 hours. The reaction was confirmed by TLC (hexane/ethyl acetate=3/1). After the reaction was completed and the precipitate was filtered off, the filtrate was concentrated under reduced pressure. The product, 2,4-trichloromethyl-(4'-bromomethylstyryl)-6-triazine (3b) was purified by a column (eluent: hexane/ethyl acetate=9/1). Yield: 4.7 g (81%).

$^1$H NMR (500 MHz, CDCl$_3$, ppm) 8.48-8.45 (1H, d, CH=), 7.71-7.69 (2H, d, ArH), 7.49-7.48 (2H, d, ArH), 7.36-7.33 (1H, d, =CH), 4.52 (2H, s, CH$_2$Br).

(3) Preparation of 2,4-trichloromethyl-(4'-formylstyryl)-6-triazine (3c)

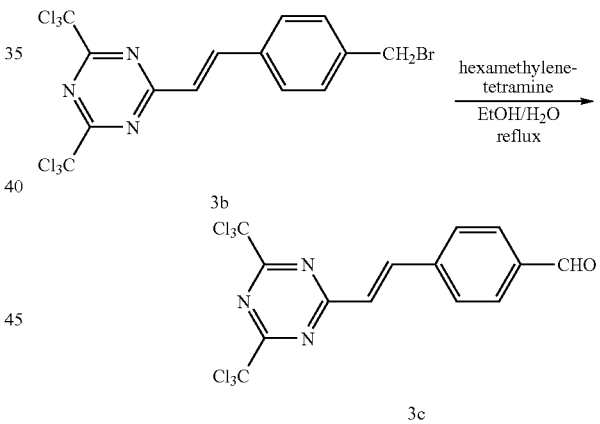

3c

Hexamethylenetetramine (0.5 g, 3.4 mmol) was, at a time, added to a solution in which the compound 3b (1 g, 1.7 mmol) was dissolved in a mixed solvent of ethanol (20 ml) or water (5 ml) to form a suspension. After the reaction mixture was stirred under reflux for 4 hours and then cooled to 5° C., hydrochloric acid (1 ml) was slowly added dropwise thereto. Then, the reaction solution was further stirred under reflux for several hours and cooled, and then poured into water. The mixture was extracted with ethyl acetate. The organic layer was dried over sodium sulfate, the solvent was removed under reduced pressure, and then the product, 2,4-trichloromethyl-(4'-formylstyryl)-6-triazine (3c) was purified by a column (hexane/dichloromethane=4/1). Yield: 0.3 g (40%).

$^1$H NMR (500 MHz, CDCl$_3$, ppm) 10.08 (1H, s, CHO), 8.53-8.49 (1H, d, CH=), 7.99-7.97 (2H, d, ArH), 7.90-7.88 (2H, d, ArH), 7.48-7.45 (1H, d, =CH).

(4) Preparation of 2,4-trichloromethyl-(4'-formyl oxime styryl)-6-triazine (3d)

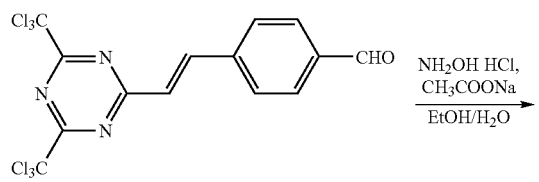

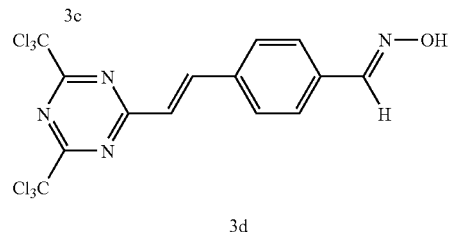

A solution of the compound 3c (1.1 g, 2.4 mmol) obtained in the above (3) dissolved in ethanol (30 ml) was added to a solution of hydroxyamine hydrochloride (0.19 g, 2.7 mmol) and sodium acetate (0.26 g, 3.2 mmol) dissolved in water (10 ml). The reaction mixture was stirred under reflux for 1 hour. The reaction was confirmed by TLC (hexane/ethyl acetate=3/1). Water (100 ml) was added to the reaction mixture. 2,4-Trichloromethyl-(4'-formyl oxime styryl)-6-triazine (3d) formed as a white solid was filtered, washed with water and then dried. Yield: 0.9 g (81%).

$^1$H NMR (500 MHz, CDCl$_3$, ppm) 11.51 (1H, s, NOH), 8.49-8.46 (1H, d, CH=), 8.16 (1H, s, H—C=N), 7.75-7.74 (2H, d, ArH), 7.68-7.67 (2H, d, ArH), 7.39-7.36 (1H, d, =CH).

(5) Preparation of 2,4-trichloromethyl-(4'-formylacetoximestyryl)-6-triazine (3)

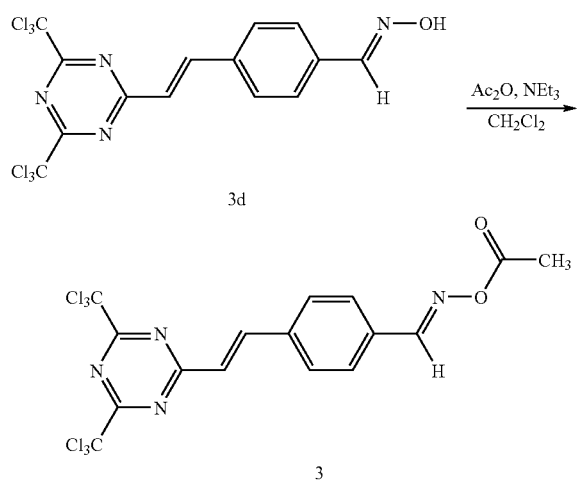

Acetic anhydride (0.39 g, 3.8 mmol) was added to a solution of the compound 3d (1.6 g, 3.5 mmol) obtained in the above (4) and triethylamine (0.38 g, 3.8 mmol) dissolved in dichloromethane (20 ml). The reaction mixture was stirred at room temperature for one day. Then, the solvent was removed under reduced pressure and the product was treated with ethanol to obtain the target compound 3. Yield: 1.3 g (76%).

$^1$H NMR (500 MHz, CDCl$_3$, ppm) 8.49-8.46 (1H, d, CH=), 8.39 (1H, s, H—C=N), 7.85-7.83 (2H, d, ArH), 7.80-7.78 (2H, d, ArH), 7.43-7.40 (1H, d, =CH), 2.26 (3H, s, (CH$_3$).

EXAMPLE 4

Preparation of 2,4-trichloromethyl-(4'-formylbiphenylacetoxime)-6-triazine (4)

(1) Preparation of 2,4-trichloromethyl-(4'-dibromomethylbiphenyl)-6-triazine (4a)

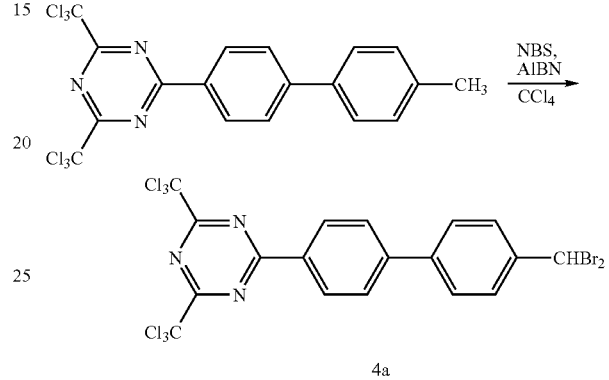

N-Bromosuccinimide (1.5 g, 8.2 mmol) and 2,2'-azobisbutyronitrile (0.1 g) were added to a solution of 2,4-trichloromethyl-(4'-methylbiphenyl)-6-triazine (trade name: TAZ-204, manufactured by Midori Kagaku Co. Ltd.) (2 g, 4.1 mmol) dissolved in carbon tetrachloride (20 ml). The reaction mixture was stirred under reflux for 2 hours. The reaction was confirmed by TLC (hexane/ethyl acetate=3/1). After the reaction was completed and the precipitate was filtered off, the filtrate was concentrated under reduced pressure. Then, the reaction product was treated with ethanol to obtain crystals of 2,4-trichloromethyl-(4'-dibromomethylbiphenyl)-6-triazine (4a). Yield: 2.2 g (84%).

$^1$H NMR (500 MHz, CDCl$_3$, ppm) 8.78-8.76 (2H, d, ArH), 7.81-7.79 (2H, d, ArH), 7.72-7.68 (4H, dd, ArH), 6.72 (1H, s, CHBr$_2$).

(2) Preparation of 2,4-trichloromethyl-(4'-formylbiphenyl)-6-triazine (4b)

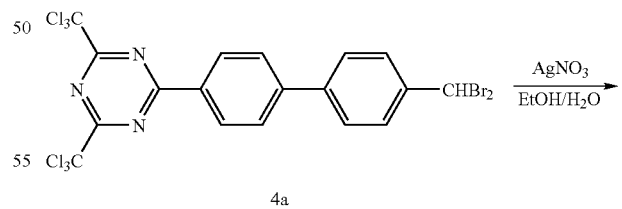

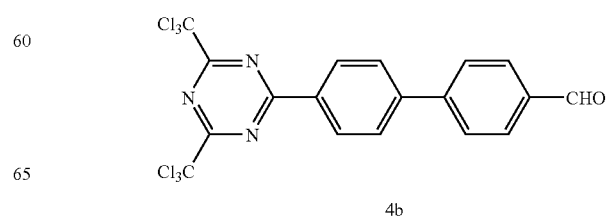

A solution of silver nitrate (0.53 g, 3.1 mmol) dissolved in water (5 ml) was added to a solution of the compound 4a (1 g, 1.5 mmol) dissolved in ethanol (20 ml). The reaction mixture was stirred under reflux for 1.5 hours. Then, the hot solution was filtered to remove the precipitate and the filtrate was cooled. The filtrate was further filtered to obtain white crystals of 2,4-trichloromethyl-(4'-formylbiphenyl)-6-triazine (4b). Yield: 0.6 g (81%).

$^1$H NMR (500 MHz, CDCl$_3$, ppm) 10.10 (1H, s, CHO), 8.81-8.79 (2H, d, ArH), 8.03-8.01 (2H, d, ArH), 7.86-7.84 (4H, d, ArH).

(3) Preparation of 2,4-trichloromethyl-(4'-formyloximebiphenyl)-6-triazine (4c)

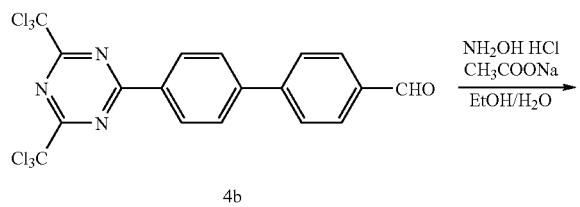

A solution of the compound 4b (1.3 g, 2.6 mmol) obtained in the above (2) dissolved in ethanol (30 ml) was added to a solution of hydroxyamine hydrochloride (0.2 g, 2.8 mmol) and sodium acetate (0.27 g, 3.3 mmol) dissolved in water (10 ml). The reaction mixture was stirred under reflux for 1 hour. The reaction was confirmed by TLC (hexane/ethyl acetate=3/1). Water (100 ml) was added to the reaction mixture. 2,4-Trichloromethyl-(4'-formyloximebiphenyl)-6-triazine (4c) formed as a white solid was filtered, washed with water and then dried. Yield: 1.1 g (84%).

$^1$H NMR (500 MHz, DMSO, ppm) 11.38 (1H, s, NOH), 8.64-8.62 (2H, d, ArH), 8.22 (1H, s, H—C=N), 8.06-8.04 (2H, d, ArH), 7.88-7.86 (2H, d, ArH), 7.76-7.74 (2H, d, ArH).

(4) Preparation of 2,4-trichloromethyl-(4'-formylbiphenylacetoxime)-6-triazine (4)

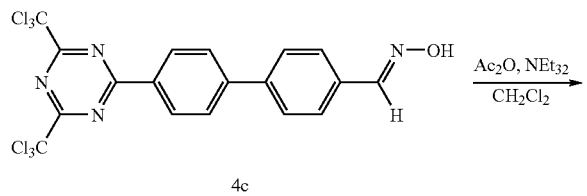

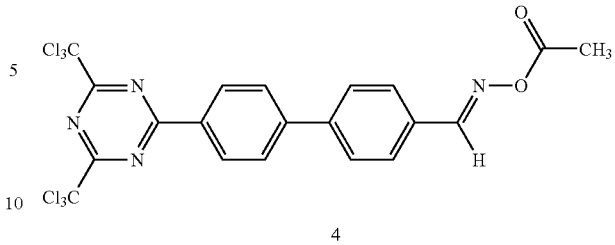

Acetic anhydride (0.24 g, 2.3 mmol) was added to a solution of the compound 4c (1.1 g, 2.1 mmol) obtained in the above (3) and triethylamine (0.23 g, 2.3 mmol) dissolved in dichloromethane (20 ml). The reaction mixture was stirred at room temperature for one day. Then, the solvent was removed under reduced pressure and the product was treated with ethanol to obtain the target compound 4. Yield: 0.8 g (68%).

$^1$H NMR (500 MHz, CDCl$_3$, ppm) 8.78-8.77 (2H, d, ArH), 8.42 (1H, s, H—C=N), 7.88-7.87 ((2H, d, ArH), 7.84-7.82 (2H, d, ArH), 7.76-7.74 (2H, d, ArH), 2.26 (3H, s, O=CCH$_3$).

EXAMPLE 5

Preparation of 2,4-trichloromethyl-(2'-acetylbiphenylacetoxime)-6-triazine (5)

(1) Preparation of 2'-acetyl-4-biphenylcarbonitrile (5a)

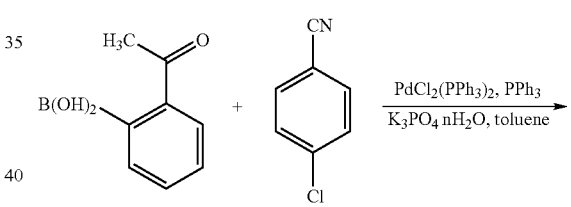

Bis(triphenylphosphine)palladium dichloride (PdCl$_2$(PPh$_3$)$_2$) (0.6 g, 0.86 mmol), triphenylphosphine (0.44 g, 1.74 mmol), (2-acetylphenyl)boronic acid (6 g, 3.76 mmol) and tripotassium phosphate hydrate (16 g, 7.54 mmol) were placed in a flask. Nitrogen was blown into the flask and then the flask was filled with toluene (40 ml) and 4-chlorbenzonitrile (4 g, 2.90 mmol). The reaction mixture was stirred at 80° C. for 4 hours. The reaction mixture was cooled and washed with water. The organic layer was dried over sodium sulfate and then the solvent was evaporated. The product, 2'-acetyl-4-biphenylcarbonitrile (5a) was purified by a column (hexane/ethyl acetate=8/1). Yield: 3.3 g (51%).

(2) Preparation of 2,4-trichloromethyl-(2'-acetylbiphenyl)-6-triazine (5b)

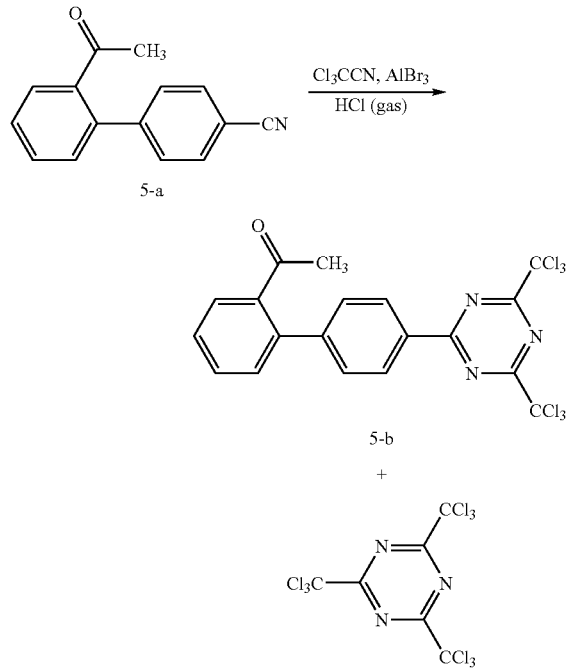

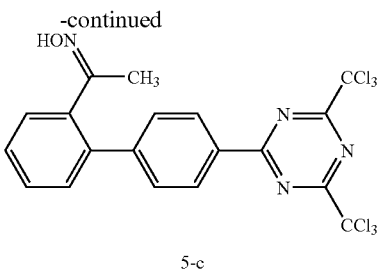

Aluminum bromide (0.5 g, 0.0019 mol) was added to a solution of the compound 5a (4.4 g, 0.019 mol) obtained in the above (1) dissolved in trichloroacetonitrile (43 g, 0.298 mol). Dry hydrogen chloride gas was passed through the reaction mixture at −10° C. for 2 hours. Then, the mixture was stirred at room temperature for one day. Trichloroacetonitrile was removed under reduced pressure. The residue was purified by a column (hexane/ethyl acetate=9/1). As a result, the mixture of 2,4-trichloromethyl-(2'-acetylbiphenyl)-6-triazine (5b) and 2,4,6-tris(trichloromethyl)-1,3,5-triazine was obtained. These two products were not separated since they have similar solubility in any solvent.

¹H NMR (500 MHz, CDCl₃, ppm) 8.79-8.75 (2H, dd, ArH), 7.65-7.64 (1H, dd, ArH), 7.59-7.58 (1H, dd, ArH), 7.56-7.55 (2H, d, ArH), 7.51-7.48 (1H, dd, ArH), 7.45-7.43 (1H, d, ArH), 2.18 (3H, s, O=CCH₃).

(3) Preparation of 2,4-trichloromethyl-(2'-acetyl oximebiphenyl)-6-triazine (5c)

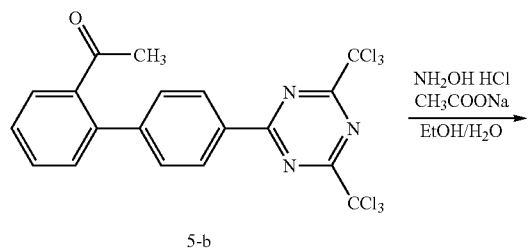

A solution of the compound 5b obtained in the above (2) and 2,4,6-tris-trichloromethyl-1,3,5-triazine (6.5 g) dissolved in ethanol (60 ml) was added to a solution of hydroxyamine hydrochloride (0.97 g, 14 mmol) and sodium acetate (1.3g, 16.5 mmol) dissolved in water (20 ml). The reaction mixture was stirred under reflux for 3 hours. The reaction was confirmed by TLC (hexane/ethyl acetate=3/1). After the reaction was completed, water (100 ml) was added to the reaction mixture. The white solid formed was filtered, washed with water and then dried. The product, 2,4-trichloromethyl-(2'-acetyl oximebiphenyl)-6-triazine (5c) was purified by a column (hexane/ethyl acetate=9/1). Yield: 1.9 g.

¹H NMR (500 MHz, CDCl₃, ppm) 8.75-8.73 (2H, d, ArH), 8.09 (1H, s, NOH), 7.63-7.61 (2H, d, ArH), 7.50-7.47 (2H, dd, ArH), 7.46-7.44 (2H, dd, ArH), 1.78 (3H, s, —N=CCH₃).

(4) Preparation of 2,4-trichloromethyl-(2'-acetylbiphenylacetoxime)-6-triazine (5)

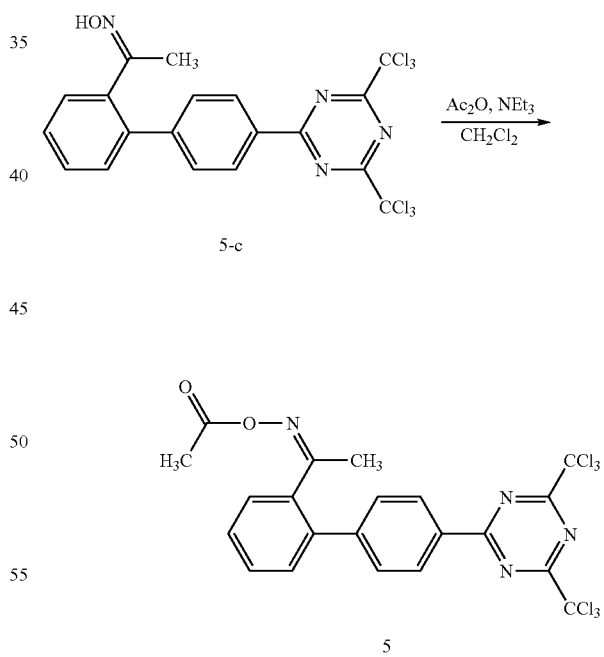

Acetic anhydride (0.4 g, 3.9 mmol) was added to a solution of the compound 5c (1.9 g, 3.6 mmol) obtained in the above (3) and triethylamine (0.4 g, 3.9 mmol) dissolved in dichloromethane (20 ml). The reaction mixture was stirred at room temperature for one day. Then, the solvent was removed under reduced pressure and the target compound 5 was purified by a column (hexane/ethyl acetate=9/1). Yield: 1.1 g (55%).

$^1$H NMR (500 MHz, CDCl$_3$, ppm) 8.75-8.74 (2H, d, ArH), 7.65-7.63 (2H, d, ArH), 7.56-7.53 (1H, dd, ArH), 7.48-7.45 (3H, m, ArH), 2.22 (3H, s, O=CCH$_3$), 1.85 (3H, s, —N=CCH$_3$).

EXAMPLE 6

Preparation of 2,4-trichloromethyl-(4'-acetylphenyloxime)-6-triazine disuccinate (6)

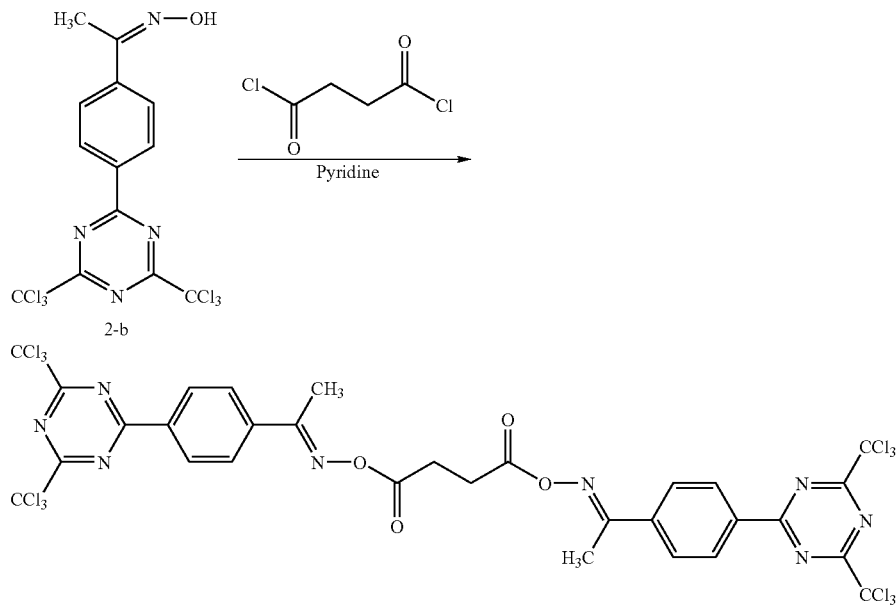

Succinyl chloride (0.45 g, 2.3 mmol) was dropped at room temperature into a solution of the compound 2b (2.0 g, 4.5 mmol) prepared in Example 2 dissolved in pyridine (40 ml). The reaction solution was stirred at room temperature for 5 hours and poured into water (300 ml). The white precipitate formed was filtered and recrystallized from ethanol. As a result, the compound of the formula 6, 2,4-trichloromethyl-(4'-acetylphenyl oxime)-6-triazine disuccinate was obtained (1.7 g, yield: 39%). The structure thereof was confirmed by NMR.

$^1$H NMR (500 MHz, CDCl$_3$, ppm)) 8.73-8.71 (2H, d, ArH), 7.95-7.98 (2H, d, ArH), 2.83 (4H, S, O$_2$CCH$_2$), 2.42 (3H, s, O=CCH$_3$), 2.28 (3H, s, —N=CCH$_3$)

What is claimed is:

1. A triazine oxime ester based photoactive compound of formula (1):

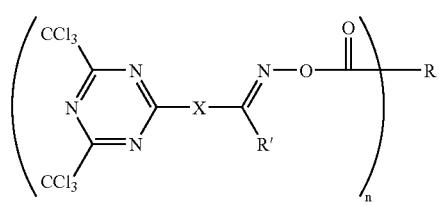

(1)

wherein n is an integer of 1 or 2;

when n=1, R is selected from the group consisting of a C$_1$ to C$_6$ alkyl group, a C$_1$ to C$_6$ haloalkyl group, a C$_1$ to C$_6$ alkyl group substituted with one or more groups selected from the group consisting of NL$_2$, OL and SL wherein L is a hydrogen atom or C$_1$ to C$_6$ alkyl group, a phenyl group unsubstituted or substituted with one or more groups selected from the group consisting of a C$_1$ to C$_6$ alkyl group, a halogen atom, a nitrile group, OH and COOH, and a C$_2$ to C$_5$ alkylcarboxyl group;

when n=2, R is selected from the group consisting of a C$_2$ to C$_6$ alkylene group, a 1,2-phenylene group, a 1,3-phenylene group, 1,4-phenylene group,

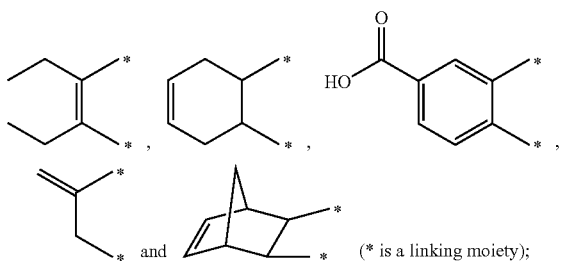

(* is a linking moiety);

R' is selected from the group consisting of a hydrogen atom, a C$_1$ to C$_6$ alkyl group, a nitrile group and a phenyl group;

X is a C$_5$ to C$_{20}$ arylene group unsubstituted or substituted with one or more groups selected from the group consisting of a halogen atom, CN, a C$_1$ to C$_6$ alkyl group, a C$_1$ to C$_6$ alkoxy group, a C$_1$ to C$_6$ alkylthio group and a morpholino group; a divalent C$_4$ to C$_{20}$ heterocyclic group containing O, N or S, unsubstituted or substituted with one or more groups selected from the group consisting of a halogen atom, CN, a $C_1$ to $C_6$ alkyl group, a $C_1$ to $C_6$ alkoxy group, a $C_1$ to $C_6$ alkylthio group and a morpholino group; or a compound of the following formula (2):

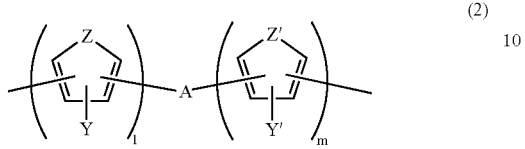

(2)

wherein Z and Z' are each independently selected from the group consisting of $CH_2$, O, S, NR'' wherein R'' is a hydrogen atom or $C_1$ to $C_6$ alkyl group, and CH=CH;

l and m are an integer of 0 to 2, provided that l+m is not 0;

A is a simple linkage, or one selected from the group consisting of $C_pH_{2p}$, $O(CH_2O)_p$, CH=CH, NR''', S, O, S=O, $SO_2$, and C=O wherein p is an integer of 1 to 6 and R''' is a hydrogen atom or $C_1$ to $C_6$ alkyl group, provided that A is not a simple linkage when l+m=1; and Y and Y' are each optionally selected from the group consisting of a hydrogen atom, a halogen atom, CN, a $C_1$ to $C_6$ alkyl group, a $C_1$ to $C_6$ alkoxy group, a $C_1$ to $C_6$ alkylthio group and a morpholino group.

2. The triazine oxime ester based photoactive compound according to claim 1, wherein in the formula (1), when n=1, R is a methyl group or a phenyl group;

when n=2, R is an ethylene group or a tetrahydrophthalene group;

R' is a hydrogen atom, a methyl group or a phenyl group; and

X is selected from the group consisting of a phenylene group, a biphenylene group, a styrylene group and the following structural formulae:

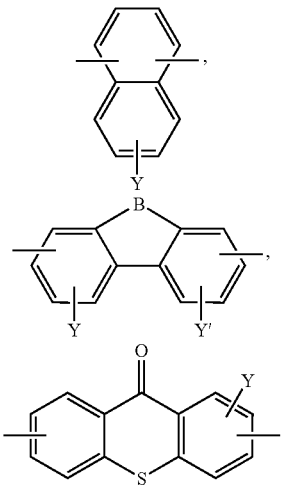

wherein B is one selected from the group consisting of $CH_2$, O, S, NR'' wherein R'' is a hydrogen atom or $C_1$ to $C_6$ alkyl group, and CH=CH; and Y and Y' are each optionally selected from the group consisting of a hydrogen atom, a halogen atom, CN, a $C_1$ to $C_6$ alkyl group, a $C_1$ to $C_6$ alkoxy group, a $C_1$ to $C_6$ alkylthio group and a morpholino group.

* * * * *